United States Patent [19]

Takayama et al.

[11] 4,222,765
[45] Sep. 16, 1980

[54] THIOLCARBAMIC ACID ESTERS

[75] Inventors: Shuichi Takayama, Shimizu; Takehito Ishikawa, Shizuoka; Ichiro Kimura, Shizuoka; Syozi Shigematu, Shizuoka, all of Japan

[73] Assignee: Kumiai Chemical Industry Co., Ltd., Tokyo, Japan

[21] Appl. No.: 913,104

[22] Filed: Jun. 6, 1978

Related U.S. Application Data

[63] Continuation of Ser. No. 763,243, Jan. 27, 1977, abandoned.

[30] Foreign Application Priority Data

Jan. 30, 1976 [JP]  Japan .................................... 51-9083

[51] Int. Cl.$^2$ ...................... A01N 9/12; A01N 21/02; C07D 295/14
[52] U.S. Cl. .................................. 71/88; 260/239 BF
[58] Field of Search ...................... 260/239 BF; 71/88

[56] References Cited

U.S. PATENT DOCUMENTS

| | | | |
|---|---|---|---|
| 2,992,091 | 7/1961 | Harman et al. | 260/239 BF |
| 3,224,861 | 12/1965 | D'Amico | 260/239 BF |
| 3,932,632 | 1/1976 | Adolphi et al. | 260/239 BF |
| 4,029,646 | 6/1977 | Aya et al. | 260/239 BF |

FOREIGN PATENT DOCUMENTS

| | | | |
|---|---|---|---|
| 2333397 | 1/1975 | Fed. Rep. of Germany | 260/239 BF |
| 51-95133 | 8/1976 | Japan | 260/239 BF |

*Primary Examiner*—Alton D. Rollins
*Attorney, Agent, or Firm*—Oblon, Fisher, Spivak, McClelland & Maier

[57] ABSTRACT

Thiolcarbamic acid esters having the formula

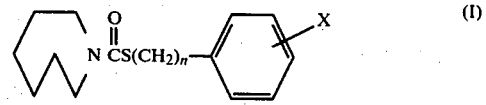

wherein X represents hydrogen or chlorine atom and n represents an integer of 2 to 3 are disclosed.

3 Claims, No Drawings

THIOLCARBAMIC ACID ESTERS

This is a continuation of application Ser. No. 763,243 filed Jan. 27, 1977, now abandoned.

BACKGROUND OF THE INVENTION

1. Field of the Invention

The present invention relates to thiolcarbamic acid esters having the formula

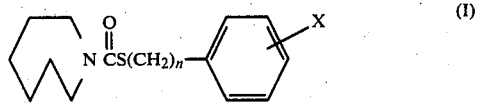

wherein X represents hydrogen or chlorine atom and n represents an integer of 2 to 3.

2. Description of the Prior Art

It has been disclosed that S-benzyl (or substituted benzyl) 1-hexamethyleneiminecarbothiolates have herbicidal effects in U.S. Pat. Nos. 3,224,861 and 3,303,014.

SUMMARY OF THE INVENTION

It is an object of the present invention to provide thiolcarbamic acid esters which have herbicidal effects to various kinds of weed by a water surface application and a soil treatment, and have long-lasting properties and have stable effects without changing the effect and safety to useful plants depending upon various conditions such as kind of soil, etc., and have low toxicity to human-body, animals, fish and shellfish. The compounds of the present invention are thiolcarbamic acid esters having the formula

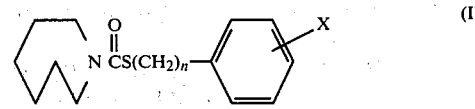

wherein X represents hydrogen or chlorine atom and n represents an integer of 2 to 3.

DETAILED DESCRIPTION OF THE PREFERRED EMBODIMENTS

The thiolcarbamic acid esters of the present invention can be referred as S-phenyl (or chlorophenyl) alkyl 1-hexamethyleneiminecarbothiolates which have remarkably higher growth controlling effect to weeds and have less phytotoxicity to rice plant in comparison with those disclosed in U.S. Pat. No. 3,224,861 and U.S. Pat. No. 3,303,014.

That is, the compounds have high intergeneric selectivity between rice plant and weeds and are remarkably advantageous in the practical use. The compounds of the invention are especially useful when applied at the young seedling stage of growth of rice plants.

The compounds of the invention have high herbicidal effect to gramineous weeds such as barnyard grass and perennial weeds such as Slenedr spikerush, *Scirpus juncoides* var. hotarui, *Cyperus serotinus Rottb, Elecocharis kuroguwai;* and broadleaf weeds such as *Monochoria vaginalis,* Toothcup, *Dopatrium junceum* Hamilt as the herbicide in paddy field. The compounds also have high herbicidal effect to gramineous weeds such as barnyard grass, *Cyperus microiria* Steud, Crab grass, Goose grass, foxtail and perennial weeds such as Purple nutsedge, Quack grass, *Oxalis martiana* ZUcc and *Rumex zaponicuo* Hotj and broadleaf weeds such as Chenopodium album L., Pig weed, *Amaranthus lividus* L, Smartweed, Common purslane and Annual fleabane, as the herbicide in up-land.

The compounds of the invention can be applied by the water surface application and the soil treatment and also by spraying or dusting on the soil to effectively control weeds.

The compounds are chemically stable and can be applied with the other component such as other herbicides, insecticides, fungicides, fertilizers and soil improvers.

The compounds of the invention can be produced by the following reaction:

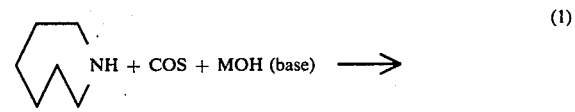

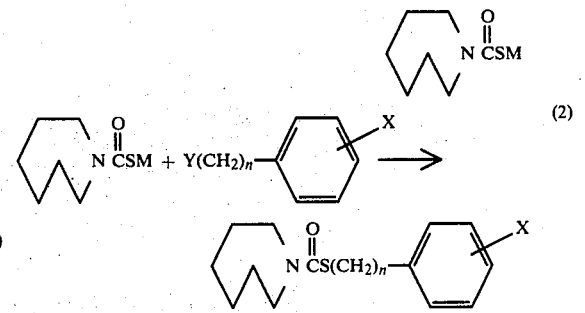

wherein M represents an alkali metal atom; Y represents a halogen atom; X represents hydrogen or chlorine atom and n represents an integer of 2 to 3.

Thus, hexamethyleneimine and a base such as sodium hydroxide or potassium hydroxide are dissolved in a solvent such as water and carbonyl sulfide is fed into the resulting solution at 0° to 20° C. preferably 15° to 20° C. whereby the salt of thiolcarbamic acid is obtained as shown by reaction formula (1).

The salt of thiolcarbamic acid is reacted with phenylalkylhalide in an organic solvent such as acetone, tetrahydrofuran, dioxane, etc. at the reaction temperature of 0° to 30° C. as shown by the reaction formula (2).

In the reaction, an equimolar amount or excess amount of carbonyl sulfide is reacted with hexamethyleneimine. The base used in the reaction is preferably an alkali metal hydroxide but can be another base such as a tert-amine. It is possible to use an excess of hexamethyleneimine as the base.

In the latter process, a large excess amount such as a double equimolar amount of carbonyl sulfide is mixed and reacted with hexamethyleneimine in an organic solvent such as acetone, tetrahydrofuran, dioxane, methanol, ethanol, benzene, toluene or xylene.

The resulting hexamethyleneimine salt of thiolcarbamic acid is further reacted with phenylalkylhalide under the same conditions to obtain the object compound as shown by the reaction formula (3).

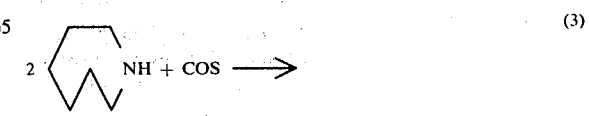

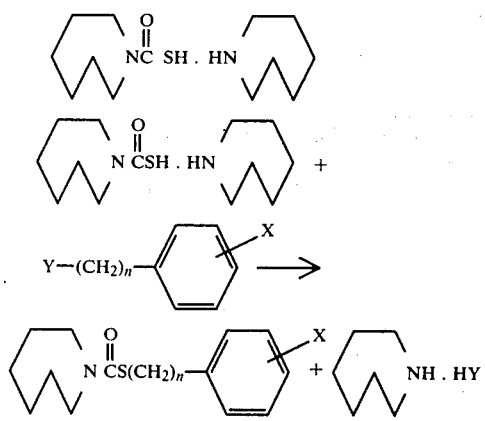

EXAMPLE 1

S-3-phenylpropyl 1-hexamethyleneiminecarbothiolate (Compound 1)

A 5.0 g (0.05 mole) of hexamethyleneimine and 2.0 g (0.05 mole) of sodium hydroxide were dissolved in 50 ml of water, and then, 1.12 liter (0.05 mole) of carbonyl sulfide was gradually fed into the aqueous solution at 5° to 10° C. After the feeding, 50 ml of acetone was added to the aqueous solution. A solution of 7.7 g (0.05 mole) of 3-phenyl propylchloride in 25 ml of acetone was added dropwise at the room temperature.

The mixture was stirred at the room temperature for 1 hour and then was stirred at the temperature refluxing acetone for 1 hour.

After the reaction, the reaction mixture was cooled to the room temperature and then was poured onto the ice water. The resulting oily product was extracted with benzene and the extract was washed with water for several times and was dried over anhydrous calcium chloride. After the drying step, calcium chloride was separated by a filtration and benzene was distilled off under a reduced pressure. The residue was distilled to obtain 10.8 g of pale yellow transparent liquid of S-3-phenylpropyl 1-hexamethyleneiminecarbothiolate having a boiling point of 143° to 147° C./0.007 mmHg (Yield: 77.7%).

EXAMPLE 2

S-2-phenylethyl 1-hexamethyleneiminecarbothiolate (Compound 2)

In accordance with the process of Example 1, the object compound was obtained by using hexamethyleneimine, carbonyl sulfide and 2-phenylethylchloride.

The object compound had the following characteristics.

Pale yellow transparent liquid
Boiling point: 139° to 142° C./0.015 mmHg
$n^D20$ 1.5650.

EXAMPLE 3

S-3-(4'-chlorophenyl)propyl 1-hexamethyleneiminecarbothiolate (Compound 3)

In accordance with the process of the Example 1, the object compound was obtained by using hexamethyleneimine carbonyl sulfide and 3-(4'-chlorophenyl)-propylchloride.

The object compound had the following characteristics.

Pale yellow platy crystal
Melting point: 41° to 46° C.

EXAMPLE 4

(Compound 3)

S-3-(4'-chlorophenyl)propyl 1-hexamethyleneiminecarbothiolate

To a solution of 10 g (0.1 mole) of hexamethyleneimine in 100 ml of toluene was introduced 1.12 liter (0.05 mole) of carbonyl sulfide at 15° to 20° C. during 30 min.

To the resulting solution was added dropwise 11.7 g (0.05 mole) of 3-(4'-chlorophenyl) propyl bromide at the room temperature during 10 min. Then, the mixture was stirred at the room temperature for 1 hour and heated at 65° to 70° C. for an additional 2 hours.

After this reaction period, the mixture was cooled to the room temperature and the deposited hexamethyleneimine hydrobromide was removed by a filtration. The filtrate was concentrated under a reduced pressure to remove the solvent.

The residue was recrystallized from hexane to obtain 10.4 g of pale yellow platy crystals having a melting point of 41° to 46° C.

These compounds are used as herbicidal composition by admixing with various adjuvants such as diluents, solvents, surface active agents, etc. in the forms of emulsifiable concentrate, wettable poweder and granules.

The compound is usually applied at a rate of 50 to 1000 g/10 ares preferably 100 to 400 g/10 ares.

The preparations of herbicidal compositions will be exemplified in detail.

The types of the active ingredients, the types of the additives and the ratio thereof are not limited to the exemplified preparations.

PREPARATION OF COMPOSITION 1

Emulsifiable concentrate

A 20 wt. parts of Compound 1, 60 wt. parts of xylene and 20 wt. parts of emulsifier of a mixture polyoxyethylene alkylphenyl ether and calcium dinaphthylmethanesulfonate (7:3) were uniformly mixed to obtain an emulsifiable concentrate. In the application, the emulsifiable concentrate was diluted with water to spray it.

PREPARATION OF COMPOSITION 2

Wettable powder

A 20 wt. parts of Compound 2, 35 wt. parts of diatomaceous earth, 40 wt. parts of talc and 5 wt. parts of spreader of sodium alkylbenzenesulfonate were mixed and pulverized to obtain a wettable powder. In the application, the wettable powder was suspended in water to spray it.

PREPARATION OF COMPOSITION 3

Powder

A 3 wt. parts of Compound 3, 47 wt. parts of talc, 47 wt. parts of clay and 3 wt. parts of silicon dioxide were mixed and pulverized to obtain a powder. In the application, the powder was applied by dusting it.

PREPARATION OF COMPOSITION 4

Granules

A 5 wt. parts of Compound 1, 15 wt. parts of bentonite, 47.5 wt. parts of talc, 30 wt. parts of clay, 2 wt. parts of sodium ligninsulfonate and 0.5 wt. part of sodium dodecylsulfonate were uniformly mixed and pulverized and then, the mixture was kneaded with 25 wt. parts of water. The mixture was granulated by an extrusion granulating machine and was dried and sieved to obtain granules. In the application, the granules are scattered.

The herbicidal effects of the compounds of the invention will be illustrated by certain experiments.

EXPERIMENT 1

Pot tests for transplanted rice and weeds in paddy field

Each porcelain pot having a diameter of 30 cm, was filled with soil containing subterranean stem (rhizome) of Slenedr spikerush, *Scirpus juncoides* Roxb var. hotarui, Arrowhead and *Cyperus microiria* Steud and then seeds of barnyard grass, *Monochoria vaginalis*, Toothcup and *Dopatrium junceum* Hamilt were sown at a ratio of 50 seeds per a pot.

Five rice seedling in two leaves stage (species: Kimmaze) were transplanted in each pot and water was poured into each pot to a depth of 3 cm.

When barnyard grass grew to one leaf stage, an aqueous emulsion prepared in the Preparation 1, was poured on the surface of water at a specific ratio.

Fourteen days after the treatment, degree of control of weeds and phytotoxicity were tested. Results are shown in Table 1.

5: Complete growth suppression is found;
4: Growth suppression compared with untreated plant is about 80%;
3: Growth suppression compared with untreated plant is about 60%;
2: Growth suppression compared with untreated plant is about 40%;
1: Growth suppression compared with untreated plant is about 20%;
0: No apparent difference between treated plants and untreated plants.

TABLE 1

| Active ingredient | Amount of active ingredient per 10 ares (g/10 ares) | Degree of control of weeds | | | | | | | Phytotoxicity to rice plant |
|---|---|---|---|---|---|---|---|---|---|
| | | A | B | C | D | E | F | G | |
| Compound (1) | 500 | 5 | 5 | 5 | 5 | 5 | 5 | 5 | none |
| | 250 | 5 | 5 | 5 | 5 | 5 | 5 | 5 | " |
| | 125 | 5 | 5 | 5 | 5 | 5 | 5 | 5 | " |
| Compound (2) | 500 | 5 | 5 | 5 | 5 | 5 | 5 | 5 | " |
| | 250 | 5 | 5 | 5 | 5 | 5 | 5 | 5 | " |
| | 125 | 5 | 5 | 5 | 5 | 5 | 5 | 5 | " |
| Compound (3) | 500 | 5 | 5 | 5 | 5 | 5 | 5 | 5 | " |
| | 250 | 5 | 5 | 5 | 5 | 5 | 5 | 5 | " |
| | 125 | 5 | 5 | 5 | 5 | 5 | 5 | 5 | " |
| Reference (1) * | 500 | 5 | 5 | 4.5 | 5 | 5 | 5 | 5 | slight |
| | 250 | 4.5 | 5 | 4 | 5 | 4.5 | 5 | 4.5 | none |
| | 125 | 4 | 4.5 | 3.5 | 5 | 4 | 4 | 4 | " |
| Reference (2) ** | 500 | 5 | 5 | 5 | 5 | 5 | 5 | 5 | slight |
| | 250 | 5 | 5 | 5 | 5 | 5 | 5 | 5 | none |
| | 125 | 4.5 | 4 | 4 | 5 | 5 | 4.5 | 4.5 | " |
| Non-treatment | — | 0 | 0 | 0 | 0 | 0 | 0 | 0 | " |

A Slenedr spikerush
B *Scirpus juncoides* Roxb var
C *Cyperus microcira* Steud
D Barnyard grass
E *Monochoria vaginalis*
F Toothcup
G *Dopatrium junceum* Hamilt Note:
Reference*

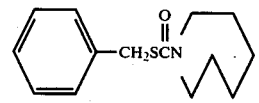 (U.S. Pat. No. 3,224,861)

Reference**

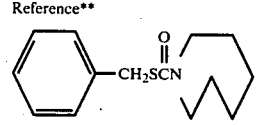 (U.S. Pat. No. 3,224,861)

EXPERIMENT 2

Pot tests for Direct sown rice and weeds in paddy field

Each porcelain pot having a diameter of 30 cm was filled with soil containing subterranean stem (rhizome) of Slenedr spikerush, *Scirpus juncoides* Roxb var. hotarui and *Cyperus microcria* Steud and then, seeds of barnyard grass, *Monochoria vaginalis*, Toothcup and *Dopatrium junceum* Hamilt were sown at a ratio of 50 seeds per a pot and rice seeds (species: Kimmaze) were sown at a ratio of 20 seeds per a pot, and water was poured into each pot to a depth of 3 cm.

When barnyard grass grew to one leaf stage, an aqueous emulsion prepared in the Preparation 3, was poured on the surface of water at a specific ratio.

Fourteen days after the treatment, degree of control of weeds and phytotoxicity were tested. Results are shown in Table 2.

TABLE 2

| Active ingredient | Amount of active ingredient per 10 ares (10/ares) | Degree of Control of Weeds | | | | | | | Phytotoxicity to rice plant |
|---|---|---|---|---|---|---|---|---|---|
| | | A | B | C | D | E | F | G | |
| Compound (1) | 500 | 5 | 5 | 5 | 5 | 5 | 5 | 5 | none |
| | 250 | 5 | 5 | 5 | 5 | 5 | 5 | 5 | " |
| | 125 | 5 | 5 | 5 | 5 | 5 | 5 | 5 | " |
| Compound (2) | 500 | 5 | 5 | 5 | 5 | 5 | 5 | 5 | " |
| | 250 | 5 | 5 | 5 | 5 | 5 | 5 | 5 | " |
| | 125 | 5 | 5 | 5 | 5 | 5 | 5 | 5 | " |
| Compound (3) | 500 | 5 | 5 | 5 | 5 | 5 | 5 | 5 | " |
| | 250 | 5 | 5 | 5 | 5 | 5 | 5 | 5 | " |
| | 125 | 5 | 5 | 5 | 5 | 5 | 5 | 5 | " |
| Reference (1) * | 500 | 5 | 5 | 4.5 | 5 | 5 | 5 | 5 | toxic |
| | 250 | 4.5 | 5 | 4 | 5 | 4.5 | 5 | 4.5 | slight |
| | 125 | 4 | 4.5 | 3.5 | 5 | 4 | 4 | 4 | none |
| Reference (2) ** | 500 | 5 | 5 | 5 | 5 | 5 | 5 | 5 | toxic |
| | 250 | 5 | 5 | 5 | 5 | 5 | 5 | 5 | slight |
| | 125 | 4.5 | 4 | 4 | 5 | 5 | 4.5 | 4.5 | none |
| Non-treatment | — | 5 | 0 | 0 | 0 | 0 | 0 | 0 | " |

Note:
The symbols are the same with those in Table 1.

What is claimed is:

1. A herbicidal compound for the control of noxious plants in paddy fields, which comprises:
a compound of the formula:

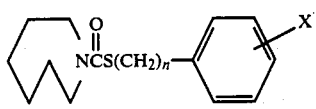

wherein
X represents hydrogen or chlorine and
n represents an integer of 2 or 3.

2. The herbicidal compound of claim 1, which is selected from the group consisting of S-2-phenylethyl-1-hexamethyleneiminecarbothiolate, S-3-phenylpropyl-1-hexamethyleneiminecarbothiolate, and S-3-(4'-chlorophenyl) propyl-1-hexamethyleneiminecarbothiolate.

3. A herbicidal composition, which comprises:
an insert carrier and a herbicidally effective amount of a thiolcarbamic ester having the formula:

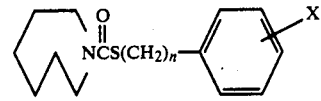

wherein X represents hydrogen or chlorine and n represents an integer of 2 or 3.

* * * * *